(12) United States Patent
Coonrod et al.

(10) Patent No.: US 10,605,728 B2
(45) Date of Patent: Mar. 31, 2020

(54) MONITORING PROBE

(71) Applicant: Halliburton Energy Services, Inc., Houston, TX (US)

(72) Inventors: Donald Scott Coonrod, Katy, TX (US); Christopher Staveley, Windsor (GB)

(73) Assignee: Halliburton Energy Services, Inc., Houston, TX (US)

( * ) Notice: Subject to any disclaimer, the term of this patent is extended or adjusted under 35 U.S.C. 154(b) by 58 days.

(21) Appl. No.: 15/764,981

(22) PCT Filed: Sep. 27, 2016

(86) PCT No.: PCT/GB2016/053004
§ 371 (c)(1),
(2) Date: Mar. 30, 2018

(87) PCT Pub. No.: WO2017/055831
PCT Pub. Date: Apr. 6, 2017

(65) Prior Publication Data
US 2018/0266947 A1   Sep. 20, 2018

(30) Foreign Application Priority Data

Oct. 2, 2015 (GB) .................................. 1517452.7

(51) Int. Cl.
*G01N 21/47* (2006.01)
*G01D 21/02* (2006.01)
(Continued)

(52) U.S. Cl.
CPC ....... *G01N 21/474* (2013.01); *G01D 5/35316* (2013.01); *G01D 21/02* (2013.01);
(Continued)

(58) Field of Classification Search
CPC .... G01N 21/474; G01N 21/412; G01N 21/45; G01N 21/954; G01N 2021/458;
(Continued)

(56) References Cited

U.S. PATENT DOCUMENTS

| 4,088,945 A * | 5/1978 | Howell ................. | G01V 3/265 324/347 |
| 2012/0193086 A1* | 8/2012 | van Dijk ................. | G01K 1/14 165/287 |
| 2015/0260607 A1* | 9/2015 | Fuller ................. | G01M 15/14 356/73.1 |

FOREIGN PATENT DOCUMENTS

| CN | 102288226 | 12/2011 |
| CN | 204679181 | 9/2015 |

(Continued)

OTHER PUBLICATIONS

Graham Wild et al., Acousto-Ultrasonic Optical Fiber Sensors: Overview and State-of-the-Art, IEEE Sensors Journal, vol. 8, No. 7, Jul. 2008, pp. 1184-1193.

(Continued)

*Primary Examiner* — Jamil Ahmed
(74) *Attorney, Agent, or Firm* — John W. Wustenberg; Baker Botts L.L.P.

(57) ABSTRACT

A monitoring probe is for monitoring a fluid inside a process system. The probe has a first portion comprising a plurality of optical sensors provided along a waveguide for monitoring a plurality of measurands from the fluid, wherein each optical sensor is configured to monitor at least one measurand from the fluid. The first portion of the probe is elongate and is configured to be inserted through an aperture of the process system into a chamber of the process system such that the optical sensors are in communication with the (Continued)

fluid. The probe further has an attachment element for securing the probe to the process system.

20 Claims, 4 Drawing Sheets

(51) Int. Cl.
  *G01N 21/41* (2006.01)
  *G01N 21/45* (2006.01)
  *G01N 21/954* (2006.01)
  *G01K 11/32* (2006.01)
  *G01D 5/353* (2006.01)
  *G01M 5/00* (2006.01)
  *G01L 1/24* (2006.01)
  *G01K 1/14* (2006.01)

(52) U.S. Cl.
  CPC ............ *G01K 1/14* (2013.01); *G01K 11/3206* (2013.01); *G01L 1/246* (2013.01); *G01M 5/0025* (2013.01); *G01M 5/0091* (2013.01); *G01N 21/412* (2013.01); *G01N 21/45* (2013.01); *G01N 21/954* (2013.01); *G01N 2021/458* (2013.01); *G01N 2021/4742* (2013.01); *G01N 2021/4769* (2013.01); *G01N 2021/9546* (2013.01); *G01N 2201/08* (2013.01)

(58) Field of Classification Search
  CPC ... G01N 2021/4742; G01N 2021/4769; G01N 2021/9546; G01N 2201/08; G01D 5/35316; G01D 21/02; G01K 1/14; G01K 11/3206; G01L 1/246; G01M 5/0025; G01M 5/0091
  See application file for complete search history.

(56) References Cited

FOREIGN PATENT DOCUMENTS

| | | |
|---|---|---|
| EP | 0438880 | 7/1991 |
| EP | 1040330 | 10/2000 |
| EP | 2502102 | 9/2012 |

OTHER PUBLICATIONS

Alan D. Kersey et al., Fiber Grating Sensors, Journal of Lightwave Technology, vol. 15, No. 8, Aug. 1997, pp. 14421463.
M. G. Xu et al., Optical In-Fibre Grating High Pressure Sensor, Electronics Letters, vol. 29, No. 4, Feb. 18, 1993, pp. 398-399.
International Search Report, PCT/GB2016/053004, dated Jan. 4, 2017.
Written Opinion, PCT/GB2016/053004, dated Jan. 4, 2017.

\* cited by examiner

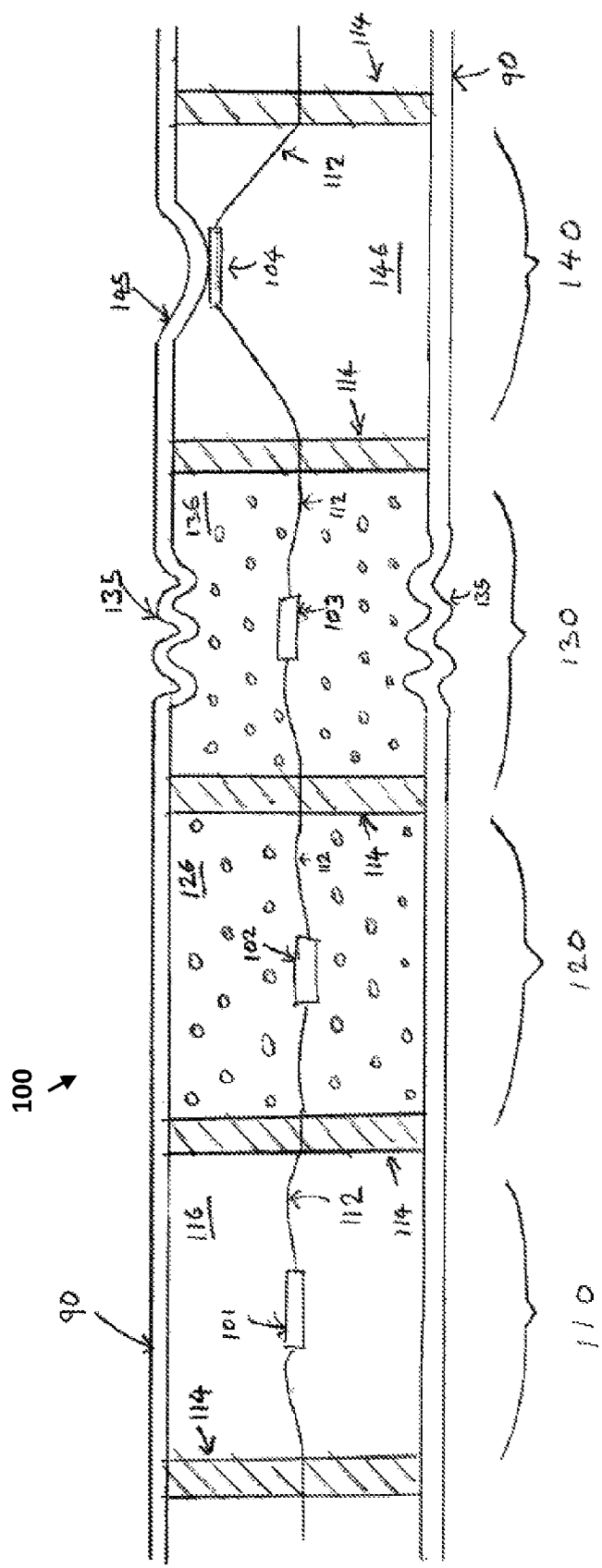

MONITORING PROBE

CROSS-REFERENCE TO RELATED APPLICATIONS

This application is the U.S. national stage application of International Application PCT/GB2016/053004, filed Sep. 27, 2016, which international application was published on Apr. 6, 2017, as International Publication WO 2017/055831 in the English language. The International Application claims priority of Great Britain Patent Application No. 1517452.7, filed Oct. 2, 2015. The international application and British application are both incorporated herein by reference, in entirety.

FIELD

The present invention relates to a probe for monitoring a fluid. Examples in which the invention finds particular benefit include the monitoring of process fluids comprising liquids and/or gas (including those containing solids) inside a system of pipes, valves, and processing equipment.

BACKGROUND

A process operator may wish to monitor any of a number of different measurands within piping arrangements such as the pressure, temperature, flow velocity, flow velocity, density and acoustic flow or process equipment operating noise. In the field of oil and gas this is often achieved by installing a plurality of instruments into a section of the piping referred to as the 'instrument hub spool piece' or 'instrument header'. Each instrument is fitted to a separate port and is placed in contact with process fluid contained within and monitors a respective parameter from it. However, it can be difficult and costly to accommodate multiple different instruments at the same cross sectional area of piping or in close proximity to process flow control equipment due to the need for multiple ports, each one with threaded or flanged connection mechanisms.

One example of where it may be desirable to monitor fluids is in order to detect the presence of leaks in piping or other process equipment. Distributed Temperature Sensing (DTS) and Distributed Acoustic Sensing (DAS) are two techniques that have been used for this purpose. In DTS, a fiber-optic cable is laid along the outside of a pipeline, or potentially in an outer annulus of the pipeline, separate from the fluid flow. A light source and a receiver are coupled to one end of the fiber optic cable. When a fluid leaks from the pipeline it comes into contact with a section of the cable and may change the temperature of this section. This temperature change can be detected by injecting light into the fiber and monitoring the spectral response from any light that is scattered back along the cable to the receiver. DTS only works however if the leaking fluid is at a different temperature than the cable. DAS works in a similar fashion however in this case it is the vibrations caused by a leaking fluid which affect the spectral response of the scattered light. By laying an optical fiber along the outside of the pipeline it is also possible to obtain pressure, temperature and strain readings from the local environment surrounding the pipeline. This may give an indication of the conditions affecting the outside of the pipeline, but is not necessarily indicative of the conditions inside the pipeline.

Additionally, neither DTS nor DAS may be sensitive enough to detect the smallest leaks. There therefore remains a need for improved methods and apparatus for monitoring fluids.

SUMMARY

In accordance with a first aspect of the invention there is provided a monitoring probe for monitoring a fluid contained inside a process system, the probe comprising:
  a first portion comprising a plurality of optical sensors provided along an optical waveguide for monitoring a plurality of measurands from the fluid, wherein each optical sensor is configured to monitor at least one measurand from the fluid;
  wherein the first portion of the probe is elongate and is configured to be inserted through an aperture of the process system into a chamber of the process system such that the optical sensors are in communication with the fluid; and
  an attachment element for securing the probe to the process system.

An improved apparatus for monitoring the characteristics of a fluid inside a process system is thus provided. Typically the fluid is a process fluid, which may comprise liquids and/or gas (including those containing solids), foam and slurry. The probe may be used with any form of process system, including a process piping system, piping/pipelines, tanks, vessel components, manifolds, flow control devices, valves, chambers, mechanical pipe joints, instrumentation rings and other ancillary processing equipment. Optical sensors are used to monitor a plurality of different measurands from the fluid. This overcomes the need to provide multiple different instruments for monitoring different parameters, wherein each instrument has its own fitting. Cost and space savings are thus achieved, as will be appreciated.

Furthermore unlike the fiber optic prior art methods previously discussed, the optical sensors are now provided on an elongate probe, which may be inserted into the fluid through an aperture into a chamber of the process system. Measurands may thus be obtained from within the process system, including from the fluid itself, rather than the environment which surrounds the outside of the process system. Furthermore the probe may be removable (i.e. separable) from the process system, meaning that the same probe may be reused at different locations on the process system, or on different process systems or components of a process system altogether. The process system may be configured to store or convey a fluid and may be either open or closed. An advantage of the probe is that its length and installation manner does not require the placement of sensors or housings inside the process system.

The sensors are configured to be placed in communication with the fluid such that they may monitor a plurality of measurands from the fluid. For example, the chamber may be configured to contain the fluid. In this case, when in use, the optical sensors may be immersed in said fluid. Alternatively the chamber may be separate from the fluid and not contain the process fluid. For example, walls of the chamber may form a physical barrier between the process fluid and the probe. An example of this is where the chamber comprises a thermowell. The optical sensors may therefore be coupled (e.g. thermally) to the process fluid but not necessarily immersed in it.

In some embodiments it is advantageous for the probe to further comprise a sealing element configured to seal the aperture so as to prevent the flow of the fluid through the aperture when the first portion is inserted therein. For example, this may be desirable when the chamber comprises the fluid as it may prevent leaks from the chamber.

A plurality of optical sensors is provided, wherein each optical sensor is configured to monitor at least one measurand from the fluid. The waveguide is preferably an optical fiber and the optical sensors are preferably fiber optic sensors. The probe may therefore comprise a length of fiber optic cable along which the optical sensors lie. Preferably still, said optical sensors preferably comprise one or more fiber Bragg gratings (FBG). FBGs are advantageous since a plurality of them may be contained within a single optical fiber, they may monitor a plurality of measurands from fluids (in particular liquids), and continue to function under high pressures and temperatures. In the oil and gas industry this may be up to about 200 MPa and 350 degrees Celsius. Instead, or in addition to the FBGs, the optical sensors may comprise one or more Long-Period Gratings, blazed or chirped fiber Bragg gratings, interferometric, spectroscopic or intensity-based sensors. The optical sensors are configured to monitor a plurality of measurands, which preferably comprise at least two of, but not limited to: pressure, temperature and acoustic noise. Most preferably, at least two sensors are provided in order to monitor pressure, temperature and acoustic noise using a combination of said sensors. Additional sensors may also be provided in order to monitor as many different measurands from the fluid as is desirable, using only a single probe. For example, the probe may further comprise one or more sensors configured to monitor any of, but not limited to: the flow velocity, water content and chemical composition of a fluid.

It is advantageous that the first portion comprises a supporting member, wherein said optical sensors are provided inside the supporting member. The supporting member may provide rigidity to the first portion, and an optical waveguide contained therein, enabling it to maintain a desired shape once inserted into a process system. Furthermore, the supporting member may protect the optical sensors from degradation due to interaction with a process fluid inside the process system. A further benefit is provided therefore wherein said supporting member comprises a closed tube defining a probe chamber, wherein said optical sensors are provided inside said probe chamber. The probe chambers may put the optical sensors into communication with the fluid outside of the closed tube in different ways. For example, an external wall of the probe chamber may comprise a flexible member for transmitting pressure from outside the probe to the optical sensors. Furthermore, said flexible member may comprise bellows for equalising the pressure between the inside and the outside of the probe chamber. A plurality of said probe chambers may be provided, wherein each probe chamber comprises an optical sensor for monitoring at least one measurand from the fluid. Each probe chamber may not necessarily be the same and may for example be filled with different fluids, or solids, for coupling the optical sensors provided therein with the walls of the tube, or may or may not comprise flexible members on the wall of the tube.

The attachment element is used for securing (and typically locking) the probe to the process system. This may be fundamentally achieved by ensuring that the attachment element cannot be inserted through the aperture in the process system. The first portion of the probe is elongate and preferably cylindrical. This preferably applies to the attachment element also, in which case the attachment element may have a larger diameter than the first portion of the probe, as defined in the direction normal to the longitudinal axis of the probe. The diameter of the first portion is preferably fractionally smaller than the aperture of the process system which it is configured to be inserted through, whereas the diameter of the fastening element is preferably larger than that of the first portion and the aperture. This prevents the entire probe from being inserted into the process system (after which it may not be retrievable). For example, the first portion of the probe may have a diameter of less than 20 mm, preferably less than 10 mm and more preferably less than 5 mm. One or more fastening members may also be provided on the attachment element for locking it to the process system. Most typically the attachment element comprises a flange or a threaded element.

The length of the first portion may depend on the size of the process system which it is configured to be inserted into. In some embodiments however the length of the first portion of the probe, along the longitudinal axis of the probe, is at least 50 mm, preferably at least 10 cm and more preferably at least 1 m. This length is preferably adjustable however to allow the probe to be fitted to a variety of differently sized components of a process system. This may be achieved by ensuring that the position along the probe at which the fastening element, and preferably the sealing element, couple to the probe is adjustable.

In some circumstances it is advantageous for the first portion of the probe to be flexible. For example the first portion may be plastically and/or elastically deformable, typically in a direction perpendicular to the longitudinal axis of the first portion. This may allow the probe to be inserted in a port having a convenient location on the outside of the process system and be deflected into a curved path by internal structures, thereby attaining a favourable final shape for making the measurement. For example, the probe may be inserted into a port on the outside of a cylindrical component of a process system, follow a straight path at a tangent to the circular bore of the component and then follow a curved internal wall of the component in the direction of the wall. The flexible probe may be exposed to the process fluid adjacent to the inner diameter of the process system component, but protected from physical damage from solids due to abrasion and physical cleaning or "pigging" of the process system using a Pipeline Inspection Gauge (PIG).

The probe preferably comprises a conductor configured to conduct signals received from the optical sensors. This conductor may be the optical waveguide, or it may be a connector configured to couple with the optical waveguide. Other means of conducting signals from optical sensors may also be desirable, including signal transmitters.

The probe is preferably removable from the process system using the attachment element. This may be achieved by reversing the process used to secure the probe to the process system in the first place, for example by removing or loosening any fastening members.

In accordance with a second aspect of the invention, there is provided a fluid monitoring system comprising:
- a process system for containing a fluid, wherein said process system comprises a chamber having an aperture; and
- a measurement probe according to the first aspect, wherein the first portion of the probe extends through the aperture and into the chamber such that, in use, the optical sensors are in communication with the fluid.

A particular benefit is provided wherein the interior of the process system is elongate, and is configured to convey a fluid along its longitudinal axis. In this case the first portion of the probe preferably extends in a direction substantially normal to the longitudinal axis of the process system. This is desirable, for example, where the fluid is configured to flow at a low velocity. In some embodiments, the process system may have a curved internal wall, in which case the probe may extend at least partially around said wall. This will ensure that the probe extends where the flow velocity is generally lowest, minimising the torque applied to the probe. This is desirable where fluid is to be conveyed along piping at a high flow velocity. The first portion of the probe is preferably flexible in order to allow it to conform to the inner wall of the process system. The inner wall may also comprise a groove configured to couple with the probe. This groove may guide the first portion of the probe as it is being inserted and may secure the probe in place, for example such that it is either flush with the inner wall or protrudes from it. This may prevent the probe from protruding significantly into the path of the flowing fluid and is desirable if there is a need to maximise flow rates or to allow devices such as PIGs to pass down the process system.

In accordance with a third aspect of the invention, there is provided a method for monitoring a fluid inside a process system comprising:

inserting a probe according to the first aspect into a process system such that the optical sensors are configured to monitor the fluid;

monitoring an optical response provided by the optical sensors;

analysing said optical response and determining one more measurands from the fluid in accordance with said analysis.

The third aspect shares similar advantages as those already discussed with reference to the first and second aspects.

BRIEF DESCRIPTION OF THE DRAWINGS

Embodiments of the invention will now be discussed with reference to the accompanying drawings, in which:

FIG. 2 is a schematic illustration of a cross sectional view of a probe in accordance with a second embodiment;

DETAILED DESCRIPTION OF THE DRAWINGS

Figure 1:
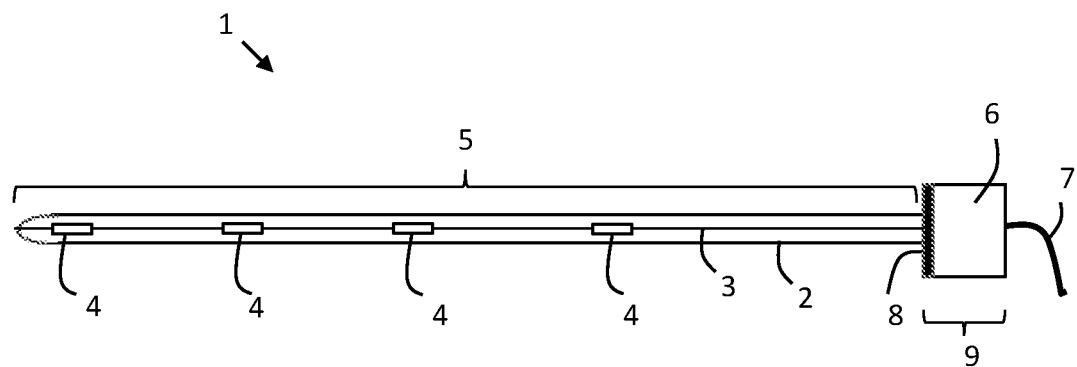
FIG. 1 is a schematic illustration of a monitoring probe in accordance with a first embodiment.

A monitoring probe 1 is shown in FIG. 1 in accordance with a first embodiment. The probe 1 is elongate and comprises a cylindrical first portion 5 and a cylindrical second portion 9 which each extend along a common longitudinal axis. The probe 1 is configured to monitor a plurality of parameters from a process fluid inside a process system. To achieve this, the entire of the first portion 5 of the probe may be inserted through an aperture in a wall of the process system, into a chamber containing the process fluid. The second portion 9 has a larger circular diameter than the aperture, preventing it from also being inserted through the aperture. The first portion 5 is thus located at the distal end of the probe 1, whereas the second portion 9 is located at the proximal end of the probe, as viewed by a user. The process fluid is the fluid which is desired to be monitored and is typically a liquid however may alternatively be a gas, or a mixture of liquid and gas. The process fluid may also further contain solids.

An optical waveguide 3 in the form of a length of optical fiber runs throughout the probe 1, along its longitudinal axis. At the first portion 5 the waveguide 3 is reinforced by a supporting member in the form of a tube 2 which encases the opticalibre 3. The supporting member may be formed of a material with a high tensile strength and may be either plastically or elastically deformable in order to allow the first portion 5 to bend if a sufficient force is applied perpendicular to the longitudinal axis of the first portion 5. Examples of suitable materials include stainless steel, nickel, titanium, cobalt, tantalum and their alloys. Alternatively the supporting member may be provided in the form of a jacket which is moulded over the waveguide 3. The supporting member 2 is formed of a durable material which will protect the waveguide 3 from degrading in the process fluid and seals the optical sensors 4 against the process fluid, thereby reducing any corrosion or wear on the sensors 4. The distal tip of the tube 2 is provided with a protective cap, which has a domed surface, in order to prevent the first portion 5 from catching when it is inserted into the process system and to stop bending loads from being applied directly to the waveguide 3.

The first portion 5 comprises a plurality of optical sensors 4 which are distally separated along the optical fiber 3. The sensors 4 are 'optical' in the sense that light that is reflected, absorbed or emitted at the sensors to monitor a measurand. Furthermore the wavelength or frequency of the light that is reflected, absorbed or emitted from the sensors may depend on this measurand. The optical sensors 4 do not receive electrical power or communicate via electrical signals. At least one optical sensor 4 is preferably provided at the distal tip of the first portion 5.

Each optical sensor 4 may monitor a different measurand from the process fluid, or alternatively one or more optical sensors 4 may be used to monitor a plurality of measurands. Furthermore, the same measurand may be monitored at different locations along the first portion 5. By providing a plurality of distally separated sensors 4 it is possible to monitor the spatial distribution of a measurand in the process fluid. The accuracy of the measurements may also be improved through the use of multiple sensors 4. A plurality of sensors 4 may also be desirable when the process fluid contains both liquid and gaseous components and measurands are desired from each. Further still, acoustic measurements at two or more locations inside the process system may help in identifying stratified flow or agglomeration of contaminants in the piping and flow control equipment, such as hydrates, paraffins and mineral scale.

In this embodiment each of the optical sensors 4 is formed of a fiber Bragg grating (FBG). An FBG is an intrinsic optical sensor recorded within the core of an optical fiber using spatially-varying patterns of intense ultra-violet laser light to create periodic modulations in a refractive index of the fiber. These modulations in the refractive index give rise to a wavelength selective mirror, whereby light travelling down the waveguide 3 is partially reflected at each of the interfaces, whilst the remaining light is transmitted through the sensor. Maximum reflectivity occurs at the Bragg wavelength, which is a property of the FBG and is dependent on both the periodicity of the refractive index and the effective refractive index of the waveguide 3. Changes in the temperature, pressure or strain at the sensor can give rise to a change in both the periodicity and the refractive index, leading to a change in the Bragg wavelength. The sensors 4 are multiplexed onto the fiber, allowing the signal emanating from each sensor 4 to be resolved at a detector.

Measurands, such as pressure, temperature or strain readings are monitored by transmitting light down the waveguide 3 and by analysing the wavelength of the light reflected from each sensor 4. Using known distributed acoustic sensing (DAS) techniques, it is also possible to monitor the acoustic noise, since this affects the strain on the optical sensors 4. By monitoring the acoustic noise (or sound) it is possible to identify the presence of any leaks in a process system, since this is typically accompanied by an increase in noise and vibrations. Other measurands may be accessed by means of specific transducers for converting changes in the desired measurand into changes in strain, temperature or pressure at the FBGs 4.

Optical sensors are advantageous since it is possible to monitor a plurality of measurands using only a single optical fiber. One optical sensor may monitor at least two or potentially three measurands. Most typically however at least two sensors monitor two or three measurands using the combination of said sensors. The probe 1 may be configured to monitor changes in any of these parameters, or may instead measure the absolute pressure, temperature or acoustic noise at the one or more sensors 4. Examples of suitable sensors are provided in EP-B1-1040330, which describes a fiber optic pressure sensor and EP-A1-2502102, which describes a birefringent micro-structured fiber optic sensor for monitoring pressure and temperature.

It is also advantageous to use optical sensors 4 since they typically have small dimensions, for example between 0.08 and 0.5 mm in diameter, meaning that the cylindrical first portion 5 may be formed with a diameter of less than 20 mm, and most preferably less than 5 mm overall. This narrow diameter enables the first portion 5, and its sensors 4, to be easily inserted through a relatively small aperture in the wall of a process system.

In other embodiments the optical sensors 4 may be any other form of sensor, such as Long-Period Gratings, blazed or chirped fiber Bragg gratings, interferometric, spectroscopic, intensity-based sensors or any combination of these (or other) types. For example in a separate embodiment one or more optical sensors 4 may be a Fabry-Pérot interferometer. One or more other sensors (which may not be optical sensors) may also be provided on the first portion 5, in order to monitor the flow velocity or water content of the fluid, or to provide spectroscopic or other chemical analysis. These sensors preferably also have a narrow diameter in order to allow them to be inserted through the aperture of the pipeline.

The probe 1 is configured to monitor parameters relating to flow conditions and flow behaviour of the fluid inside process piping. These parameters can be static, quasi-static or dynamic. These terms refer to how the difficulty of following measurand changes is affected by the time taken to make the changes. Static parameters do not change with time. Quasi-static parameters change with time but not so quickly that the measurement is distorted from the equivalent static value. Dynamic parameters however change quickly with time, giving rise to measurement values that may vary significantly from the equivalent static ones, depending on how the measurement is made. A sensor may need to be designed specifically for the dynamic measurement condition, e.g. one with a faster response or higher resonant frequency than for static measurements. For example, static pressure is a common process measurement and can be used to infer flow rates, whereas dynamic pressure can be used to pick up small fluctuations caused by pumps, allowing the operation and the condition of the pump to be monitored. These parameters may be monitored using different sensors in the same probe.

The first portion 5 is inserted through the aperture into a chamber of the process system until the sealing element 8 abuts onto the outer wall of the process system. An attachment element 6 is then used to secure the probe to the process system. The sealing element 8 prevents the flow of fluid through the aperture and may, for example, be a rubber washer, an o-ring, a c-ring or a gasket. The attachment element 6 comprises fastening members, which may include a bolt or screws (for example) or a threaded section, which are used to tighten the attachment element against the sealing element and the outer wall of the process system. The seal may be designed so that the primary seal(s) can be tested for integrity via a proof test port.

Alternatively the sealing element 8 could be formed of a swellable material which is configured to expand inside the aperture, thereby sealing it. Furthermore the attachment and the sealing element may potentially be unitary. For example, the attachment element may include a screw portion, a conical ferrule, or a male or female cone for coupling with a corresponding part provided at the aperture. The fastening element may therefore seal the aperture by securing the probe to the process system, without the need for a separate sealing element.

The optical fiber 3 is attached to distal and proximal ends of the tube 2 and through the second portion 9, trailing from the probe in the form of a flying lead 7. The flying lead 7 acts as a conductor for transmitting data to and from the sensors 4. Instead of a flying lead 7, a plug socket or connector may be provided for engaging with a suitable cable, or any other form of data transmitter. The plug socket or connector may equally be contained within and accessible from the proximal end of the second portion 9 to protect it from mechanical damage.

The probe 1 may be inserted through and removed from multiple different apertures in a process system in order to monitor a plurality of measurands from a fluid inside the process system at respective locations. This prevents the need for numerous different instruments to be provided, each for monitoring a single measurands at fixed locations. Furthermore, the probe is relatively simple and cheap to both manufacture and install, which is also advantageous.

The sensors 4 may be enclosed in a vacuum inside the tube 2 or surrounded by a fluid, such as a gas or liquid, or potentially by solid matter. Each sensor 4 is in communication with the surrounding environment outside of the tube 2 for monitoring measurands outside of the tube 2. This may be achieved in a number of different ways, examples of which will be discussed below.

A second embodiment of a probe 100 is shown in FIG. 2, wherein a cross-sectional view of part of a first portion of a probe 100 has been taken along the longitudinal axis of the probe 100. An optical waveguide 112 extends inside a flexible thin walled tube 90 and comprises a plurality of optical sensors 101, 102, 103 and 104, distributed along its length. The first portion is divided into a plurality of probe chambers 110, 120, 130 and 140, wherein an optical sensor is provided inside each probe chamber. The probe chambers are separated from one another by sealing members 114 formed of an elastomer, polymer (such as an epoxy resin), or a metal or glass solder element which isolate the probe chambers and prevent fluid transmission between them. In each case the sealing members 114 and the inner surface of the tube 90 define the size of the respective probe chambers. The optical waveguide 112 extends continuously through each of the probe chambers and the sealing members 114.

In the first probe chamber 110, the sensor 101 is contained inside a vacuum 116 and is in thermal communication with the outside of the tube 90 by radiation and conduction along the waveguide only. The sensor 101 is isolated from mechanical effects, including thermal expansion of the tube 90 and can be used for calibrating measurements obtained from other sensors, or for monitoring the average temperature of the process fluid.

The second probe chamber 120 substantially matches the first chamber 110 except that it is filled with an acoustic or thermal coupling medium 126 such as a liquid, gel or elastomer. This medium 126 enables stress waves to be transmitted from the tube 90 to the sensor 102 for monitoring acoustic signals, and provides improved thermal coupling between the sensor 102 and the process fluid.

In the third probe chamber 130 of the probe 100, part of the tube 90 is replaced with bellows 135 which extend circumferentially around the probe 100. An incompressible fluid 136 is provided inside the third chamber 136 for coupling the sensor 103 with the bellows 135. The bellows 135 act to equalise the pressure between the inside and the outside of the tube 90. Pressure, temperature and noise measurands may be monitored using this chamber 130.

In the fourth probe chamber 140 a region of the tube 90 is formed of a diaphragm 145, whilst the interior of the chamber 140 comprises an inert gas 146 or a vacuum. The diaphragm 145 is configured to deform and flex depending on the pressure acting on it from outside the tube 90. An optical sensor 104 is attached to the diaphragm 145, inside the fourth chamber 140. The sensor 104 is configured to monitor pressure or acoustic waves based on the strain applied to it by this deformation.

Since different probe chambers could be provided to monitor different measurands, each probe chamber could in effect be treated as a separate sensor. It should be understood that any number, combination or order of different probe chambers may be provided for achieving different couplings between an internal optical sensor and the environment outside of the probe, and for monitoring different measurands.

Furthermore in some examples the optical or non-optical sensors of the probe may be placed in physical contact with the process fluid.

In the following examples the probe is fitted to a component of a process system in the form of a pipe joint. The probe may be fitted to a variety of process systems and process system components however, as previously described.

Figure 3:
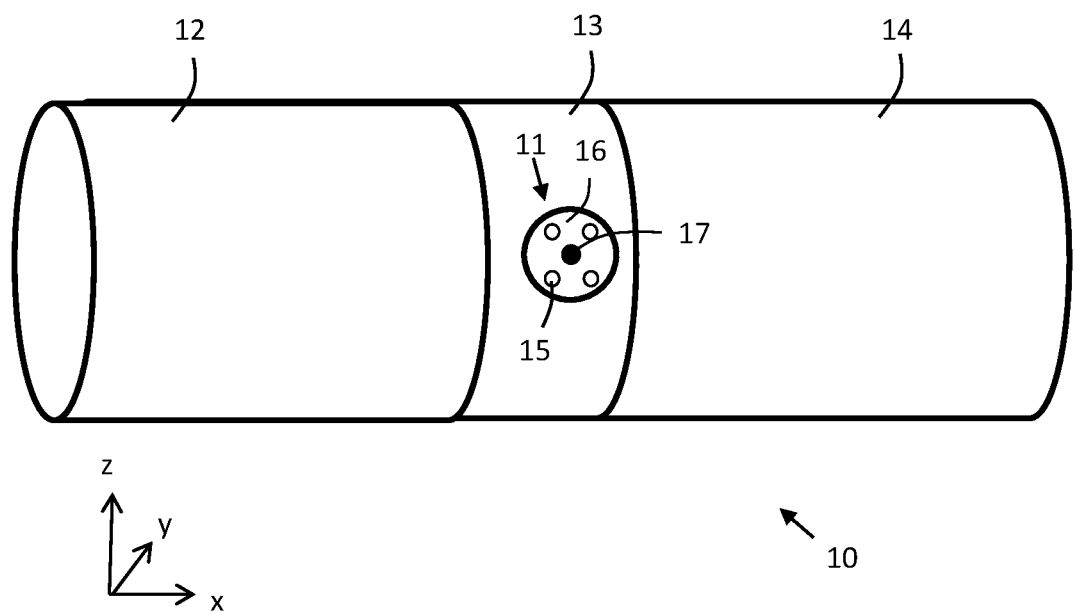
FIG. 3 is a schematic illustration of a fluid monitoring system in accordance with a third embodiment.

FIG. 3 illustrates a third embodiment wherein a perspective view is shown of the outside of a pipe 10 having a monitoring probe 11, installed within it for monitoring a process fluid contained within the pipe 10. The monitoring probe 11 shown here is similar to that of the first embodiment. Coordinate axes are also provided in FIG. 3 for reference, in which the abscissa x-axis is parallel to the longitudinal (major) axis of the pipe 10 and therefore parallel to the flow path of any fluid contained therein. The ordinate y-axis and the z-axis are each mutually perpendicular and are perpendicular to the x-axis.

The probe 11 is fitted to a pipe section 13 which connects two neighbouring elongate pipe sections 12, 14. The pipe section 13 forms part of a chamber which is configured to contain a process fluid. Piping is typically manufactured to standard sizes which are designed and qualified for a particular pressure/temperature combination. It may be undesirable to drill an aperture into a 'standard' section of piping since this may affect its ability to store or convey fluid at the desired pressure and temperature. It is advantageous therefore to install the probe to a special section of the pipe which is designed to accommodate a probe. In one advantageous arrangement, the probe 11 is installed to a pipe section, such as an instrument spool piece, which is connected between two standard flange joints. Because the first section is small, it could be fitted in between the flanges of a standard flanged joint, in a specially made piece that fits like a gasket. Alternatively, the probe may wrap around the inner circumference of a mechanical pipe connector, in the center of the connector (where the inner diameter is larger than the adjacent pipes). This prevents the probe from intruding substantially into the process fluid flow path. It is beneficial to install the probe 11 next to a valve in order to check whether the valve is leaking, open, closed or partially choked. It is also advantageous to monitor the build-up of sediments at these locations.

In this embodiment however the first portion of the probe 11 is inserted through an aperture in the wall of the pipe joint 13 and extends linearly through the midpoint of the pipe joint 13, into the process fluid. The aperture is formed in the outer wall of the pipe, which defines the inside of the pipe, and extends from outside the pipe through to the inside of the pipe. The probe 11 is secured to the pipe joint 13 by four fastening members 15 in the form of bolted screws that tighten the attachment element 16 onto the outer wall of the pipe joint 13. In this embodiment the attachment element is a flange which couples with the outer wall of the pipe. A flying lead exits the probe 11 and enables data to be transmitted to and from the optical sensors.

In alternative embodiments the position of the sealing element and the attachment element along the probe may be adjustable so as to either increase or decrease the section of the probe which may be inserted to the pipe (i.e. to adjust the length of the first portion). This enables the length of the probe to be adjusted depending on the diameter of the pipe.

Figure 4:
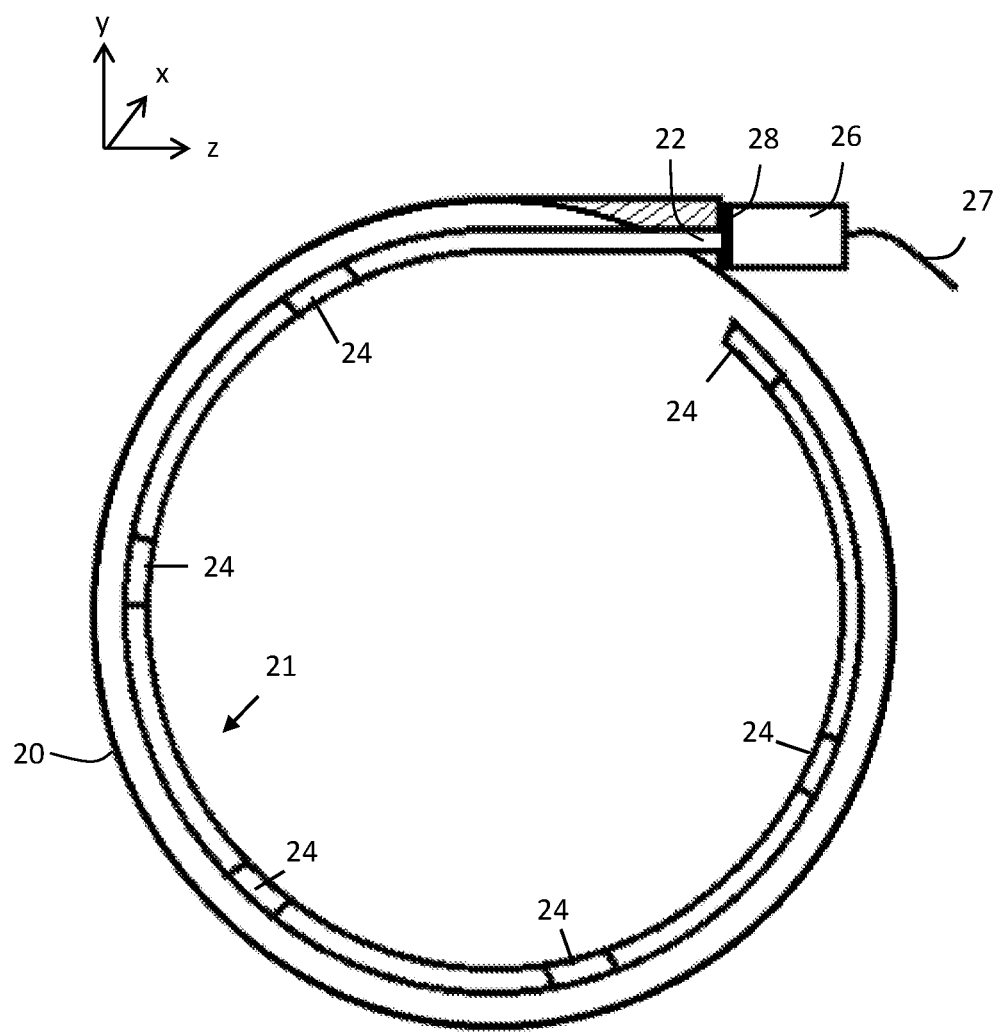
FIG. 4 is a schematic illustration of a cross-sectional view of fluid monitoring system in accordance with a fourth embodiment.

FIG. 4 illustrates the interior of a pipe 20 with a monitoring probe 21 installed within it in accordance with a fourth embodiment. A cross-section has been taken in this instance through the y-z plane, perpendicular to the longitudinal axis of the pipe 20. In this embodiment the inner wall of the pipe 20 is circular in cross-section however the external wall, whilst substantially circular also, has a stepped feature configured to engage with the attachment element 26 of the probe 21. The first portion is inserted through an aperture 22, which is formed in the stepped section, at a tangent to the circular cross-section of the pipe 20. As with the previous embodiments, a sealing element 28 is provided for sealing the aperture 22 when the first portion of the probe 21 has been fully inserted. In this embodiment the sealing element 28 is an O-ring located which is adhered to the attachment element 26 and configured to engage with the outer wall of the pipe surrounding the aperture 22.

An optical fiber also extends from the distal tip of the first portion, through the attachment element 26 and trails from the probe 21 as a flying lead 27, which is connected to a light source and a receiver (not shown). The first portion of the probe 21 is flexible and comprises six FBG sensors 24 which are separated along a length of reinforced optical fiber.

Figure 5:
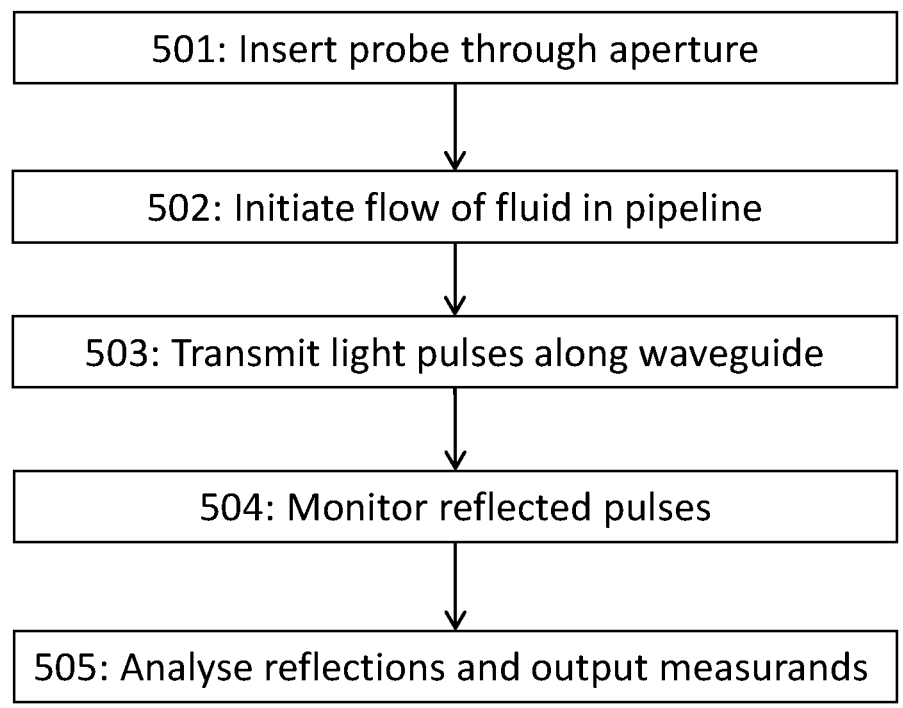
FIG. 5 is a flow diagram of a method for monitoring a fluid inside a process system in accordance with a fifth embodiment of the invention.

A method for monitoring a plurality of parameters from a fluid in a process system will now be discussed with reference to the flow diagram of FIG. 5 and the apparatus of FIG. 4.

The method begins at step 501 wherein the first portion of the probe 21 is inserted through an open aperture 22 in an empty pipe 20. Although the first portion is initially straight, as the probe 21 is inserted, it abuts onto the inner circumferential wall of the pipe 20 and is deformed either elastically or plastically and elastically, causing it to coil about the longitudinal axis of the pipe 20, following the arc of a circle. The first portion of the probe 21 preferably follows an arc of between 180 to 360 degrees, more preferably between 200 to 300 degrees, in a direction perpendicular to the longitudinal axis of the pipe section in which the probe 21 is inserted.

In this instance the inner surface of the pipe 20 comprises a groove (not shown) which is configured to couple with the first portion, so as to guide the probe and hold it in position. The groove is preferably configured such that the first portion is flush with the inner circumferential wall in order to minimise the force applied to the first portion by the process fluid. The first portion is inserted through the aperture 22, along the groove, until the sealing element 28 engages with the outer wall of the pipe. The attachment element 26 comprises screws which engage with the outer wall of the pipe and are tightened so as to press the sealing element 28 onto the aperture 22 and form a seal. This method of securing the probe 21 prevents the need to rotate the probe itself. This would otherwise be difficult to achieve if the first portion of the probe 21 has already formed a coiled arrangement inside the pipe.

Process fluid is then allowed to flow through the pipe 20 at step 502. In principle any process fluid may be used however most typically it is a liquid. In this example the pipe 20 is entirely filled with liquid that flows along the longitudinal x-axis of the pipe and surrounds each of the FBG sensors 24. The coiled arrangement of the probe 21 inside the pipe 20 ensures that the probe does not substantially intrude the flow (which is often strongest through the center of the pipe).

The sensors 24 are then interrogated using known techniques in order to monitor a plurality of measurands from the sensors 24. A light source and a receiver (not shown) are provided outside of the pipe 20 and are coupled to the waveguide 27. In this example a broadband light source is used to transmit a plurality of light pulses at step 503 along the waveguide 27, 3. When the light reaches each FBG grating 24 a proportion of the emitted light is reflected back along the waveguide 3, 27, in an opposite direction to the emitted pulse. The reflected light is monitored at step 504 by a receiver in the form of a spectrometer. The signals received from each sensor 24 can be differentiated between one-another based on the time of flight between the emitted and reflected pulses. This technique is referred to as time domain multiplexing.

The reflections are then analysed by the spectrometer at step 105. For example, the wavelengths of the reflected pulses are detected. Each FBG sensor will reflect light at a characteristic wavelength for that sensor at a given pressure or temperature. If the probe 21 has been calibrated, a measurand can then be detected from the wavelength shift in the returning signal using known techniques. An example of how to monitor pressure using an optical sensor is shown in M. G. Xu, L. Reekie, Y. T. Chow, J. P. Dakin, *Electron. Lett.* Vol. 29, No. 4 398-399 (1993). An example of how to monitor temperature using an optical sensor is shown in Kersey, A, Davis, M. A. Patrick, H. J. Leblanc, M. Koo, K. P. Askins, C. G. Putnam, M. A. Friebele, E. J., *J. Lightwave Tech.*, Vol. 15 No. 8 1442-1463, (1997). Furthermore examples of how to monitor acoustic noise using an optical sensor are shown in Wild, G. and Hinckley, S., *Sensors Journal*, Vol 8, Iss. 7. IEEE, 1184-1193 (2008).

The probe 21 may later be removed from the device by emptying the pipe section to which it is fixed of process fluid, unfastening the attachment element 26 and withdrawing the probe 21 from the aperture 22. If the first portion of the probe 21 is reinforced by an elastically deformable material it should revert to its original straight line shape and will be ready to be inserted once more into another aperture. Alternatively, if the sensors are installed into a chamber of the process system in the form of a thermowell, the thermowell will prevent process fluid from escaping through the aperture when the probe is removed and so it is not necessary to empty the pipe of the process fluid. Similarly, the sensors may be deployed in another chamber in the form of a blind hole in a valve body or a mechanical connector, which may comprise a flexible member, such as bellows or diaphragm, for transmitting pressure from the process fluid to the probe meanwhile preventing the process fluid from coming into direct contact with the sensors.

As will be appreciated, an improved monitoring probe is therefore provided for monitoring a plurality of measurands of a fluid in a process system. This probe may be used with components of a process system for storing or conveying virtually any fluid, however it may be particularly advantageous in the field of oil and gas where it is important to obtain measurands from hydrocarbons, such as crude oil, that are transported along pipes (also referred to as pipelines). Optical sensors, such as FBGs are also particularly effective at operating in the pressure and temperature ranges often associated with this industry.

For example, the probe may be used to monitor the pressure and temperature upstream and downstream of valves and chokes to check they are operating correctly. Alternatively it could be used for monitoring valves for acoustic events which could indicate leaks too small to create measurable pressure or temperature changes. Similarly it could be used for checking the function of pumps, compressors, hydraulic machinery and sealing components by measuring and analysing pressure, temperature and acoustic signals. It could be used for monitoring the function and condition of pumps and other machinery via measurement of their acoustic signals and analysis. Additional non-optical sensors may also be provided along the probe however for monitoring a number of different parameters, such as the chemical composition, flow velocity and water content of the process fluid, in order to further increase its utility.

Examples of use of this apparatus are for direct measurements of process fluid physical attributes in direct proximity with optical/non-optical sensors and indirect measurements of dynamic properties using the process fluid, probe, and mechanical acoustic conductivity to conduct acoustic vibrations to a sensor.

The apparatus may use the close proximity of a sensor to specific locations of measurements to provide a physical correlation between the installed location of the probe and the measurement at the probe.

Prior art methods utilising fiber optics for remote measurement incorporate a means of injecting light into the fiber and monitoring the spectral response and at a time-of-flight window to measure temperature or strain artefacts on the fiber. As the time-of-flight of the light is dependent on the length of the fiber circuit, it is necessary to calibrate the location of the measurement after installation of the complete fiber optic circuit, otherwise the location of the measurement is not precisely known. Location calibration methods have yet to be identified in such practices.

Precise physical location of the measurement is desirable for direct measurements at specific points in a process flow. It is also desirable for indirect measurements at specific points relative to process equipment arrangement of operation for purposes of, but not limited to, leak detection across pressure barriers such as pipe connections, valves, pumps, and vessels.

For purposes of condition monitoring, it is desirable that the number of artefacts influencing analysis are reduced. Indeterminacy of measurement location significantly degrades the ability to analyse process equipment operation and condition.

The need for measuring properties at precise locations in a process system, independent of installed fiber length and topology requires a cost-effective alternative method of correlating the physical measurement location with the measurement technique. The method should be immune to measurement point inaccuracies and indeterminacy due to changes in measurement topology or fiber lengths over the service life of the process. This is provided by the above described apparatus, system and method.

The invention claimed is:

1. A monitoring probe for monitoring a process fluid contained inside a process system, the monitoring probe comprising:
    a first portion comprising a plurality of optical sensors provided along an optical waveguide for monitoring a plurality of measurands from the process fluid,
        wherein each of the plurality of optical sensors is configured to monitor at least one measurand from the process fluid,
        wherein said first portion comprises a supporting member comprising a closed flexible tube defining a plurality of probe chambers,
        wherein the plurality of optical sensors extend continuously through the plurality of probe chambers,
        wherein the plurality of probe chambers are configured to physically separate the plurality of optical sensors from the process fluid,
        wherein the first portion of the monitoring probe is elongate and is configured to be inserted through an aperture of the process system into a chamber of the process system such that the optical sensors are in communication with the process fluid;
    a sealing element configured to seal the aperture so as to prevent the flow of the process fluid through the aperture when the first portion is inserted therein; and
    an attachment element for securing the monitoring probe to the process system, wherein the attachment element has a larger diameter than the first portion of the monitoring probe, as defined in the direction normal to the longitudinal axis of the monitoring probe, and the attachment element comprises a fastening element for locking the monitoring probe to the process system.

2. The monitoring probe according to claim 1, wherein said optical sensors are fiber optic sensors.

3. The monitoring probe according to claim 1, wherein said optical sensors are selected from a group consisting of: fiber Bragg gratings, Long-Period Gratings, blazed or chirped fiber Bragg gratings, interferometric, spectroscopic and intensity-based sensors.

4. The monitoring probe according to claim 1, wherein said plurality of measurands comprise at least two of: pressure, temperature, and acoustic noise.

5. The monitoring probe according to claim 1, further comprising one or more sensors configured to monitor any of: the flow velocity, water content, and chemical composition of a process fluid.

6. The monitoring probe according to claim 1, wherein an external wall of at least one of the probe chambers comprises a flexible member for transmitting pressure from outside the monitoring probe to the optical sensors.

7. The monitoring probe according to claim 6, wherein said flexible member comprises bellows for equalising the pressure between the inside and the outside of at least one of the probe chambers.

8. The monitoring probe according to claim 1, wherein each of the plurality of probe chambers comprises one of the plurality of optical sensors.

9. The monitoring probe according to claim 1, wherein each of the plurality of probe chambers is filled with another fluid or a solid so as to couple the plurality of optical sensors with a wall of the closed flexible tube.

10. The monitoring probe according to claim 1, wherein the monitoring probe is removable from the process system using the attachment element.

11. A fluid monitoring system comprising:
    a process system for containing a process fluid, wherein said process system comprises a process chamber having an aperture; and
    a measurement probe comprising:
        a first portion comprising a plurality of optical sensors provided along an optical waveguide for monitoring a plurality of measurands from the process fluid,
            wherein each of the plurality of optical sensors is configured to monitor at least one measurand from the process fluid,
            wherein said first portion comprises a supporting member comprising a closed flexible tube defining a plurality of probe chambers,
            wherein the plurality of optical sensors extend continuously through the plurality of probe chambers,
            wherein the plurality of probe chambers are configured to physically separate the plurality of optical sensors from the process fluid,
            wherein the first portion of the measurement probe is elongate and is configured to be inserted through the aperture of the process system into the process chamber such that, in use, the optical sensors are in communication with the process fluid;
        a sealing element configured to seal the aperture so as to prevent the flow of the process fluid through the aperture when the first portion is inserted therein, and
        an attachment element for securing the measurement probe to the process system, wherein the attachment element has a larger diameter than the first portion of the measurement probe, as defined in the direction normal to the longitudinal axis of the measurement probe, and the attachment element comprises a fastening element for locking the measurement probe to the process system.

12. The system according to claim 11, wherein the process system has a curved internal wall, wherein said first portion extends at least partially around said curved internal wall.

13. The system according to claim 12, wherein said curved internal wall comprises a groove configured to couple with the measurement probe.

14. The system according to claim 11, wherein the measurement probe is configured to monitor the flow of the process fluid inside the process system.

15. The system according to claim 11, wherein the process chamber is configured to contain the process fluid when in use.

16. The system according to claim 11, wherein the process chamber is a thermowell.

17. A method for monitoring a process fluid inside a process system comprising:
inserting a monitoring probe into a process system such that the optical sensors are configured to monitor the process fluid, wherein the monitoring probe comprises:
a first portion comprising a plurality of optical sensors provided along an optical waveguide for monitoring a plurality of measurands from the process fluid,
wherein each of the plurality of optical sensors is configured to monitor at least one measurand from the process fluid,
wherein said first portion comprises a supporting member comprising a closed flexible tube defining a plurality of probe chambers,
wherein the plurality of optical sensors extend continuously through the plurality of probe chambers,
wherein the plurality of probe chambers are configured to physically separate the plurality of optical sensors from the process fluid,
wherein the first portion of the monitoring probe is elongate and is configured to be inserted through an aperture of the process system into a chamber of the process system such that the optical sensors are in communication with the process fluid;
a sealing element configured to seal the aperture so as to prevent the flow of the process fluid through the aperture when the first portion is inserted therein, and
an attachment element for securing the monitoring probe to the process system, wherein the attachment element has a larger diameter than the first portion of the monitoring probe, as defined in the direction normal to the longitudinal axis of the probe, and the attachment element comprises a fastening element;
locking the monitoring probe to the process system using the fastening element;
monitoring an optical response provided by the optical sensors; and
analyzing said optical response and determining one or more measurands from the process fluid in accordance with said analysis.

18. The monitoring probe according to claim 1, wherein each of the plurality of probe chambers is filled with another fluid or a solid so as to couple the plurality of optical sensors with a wall of the closed flexible tube.

19. The method of claim 17, wherein the one or more measurands comprise at least two of: pressure, temperature, and acoustic noise.

20. The method of claim 17, further comprising: monitoring any of: the flow velocity, water content, and chemical composition of a process fluid.

\* \* \* \* \*